United States Patent [19]

Udo et al.

[11] Patent Number: 5,164,068
[45] Date of Patent: Nov. 17, 1992

[54] OXYGEN SENSOR

[75] Inventors: Shohei Udo, Anjo; Hiromi Sano, Nagoya; Katsuhiro Ishikawa, Aichi, all of Japan

[73] Assignee: Nippondenso Co., Ltd., Kariya, Japan

[21] Appl. No.: 667,399

[22] PCT Filed: Aug. 2, 1990

[86] PCT No.: PCT/JP90/00983
§ 371 Date: May 15, 1991
§ 102(e) Date: May 15, 1991

[87] PCT Pub. No.: WO91/02245
PCT Pub. Date: Feb. 21, 1991

[30] Foreign Application Priority Data

Aug. 8, 1989 [JP] Japan ............... 1-205098

[51] Int. Cl.⁵ ............................................. G01N 27/26
[52] U.S. Cl. .................................. 204/424; 204/426; 204/428; 204/429
[58] Field of Search ............... 204/424, 426, 428, 429, 204/153.1

[56] References Cited

U.S. PATENT DOCUMENTS 3,989,614 11/1976 Tien .
4,282,080 8/1981 Muller et al. ................ 204/428
4,300,990 11/1981 Maurer .
4,334,974 6/1982 Muller et al. ................ 204/426

FOREIGN PATENT DOCUMENTS 61-51557 3/1986 Japan .
62-222159 9/1987 Japan .

Primary Examiner—John Niebling
Assistant Examiner—Bruce F. Bell
Attorney, Agent, or Firm—Cushman, Darby & Cushman

[57] ABSTRACT

The present invention relates to an oxygen sensor, in which in order to be strong against vibration and shocks as well as to make rapid heating possible and to be capable of rapidly performing correct detection, the oxygen sensor provided is composed of a sensor element having a body portion and a thin portion which is thinner than the body portion, a detecting element is formed at the thin portion for measuring oxygen concentration, and an exothermic element is provided for heating the detecting element.

8 Claims, 5 Drawing Sheets

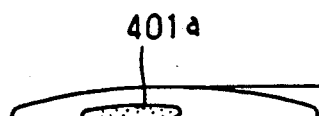
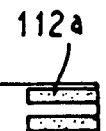
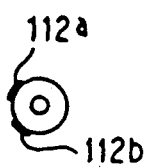
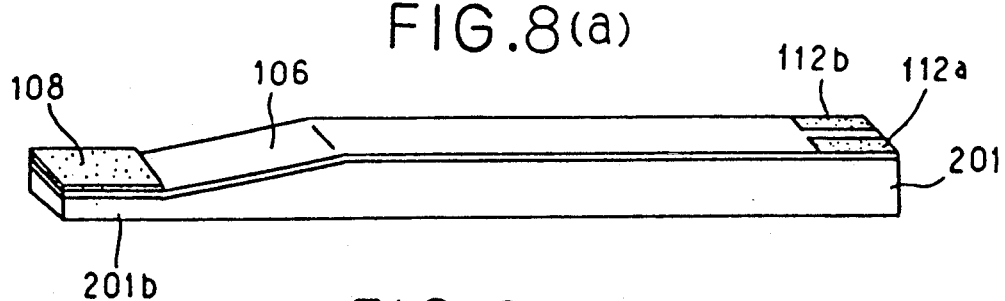
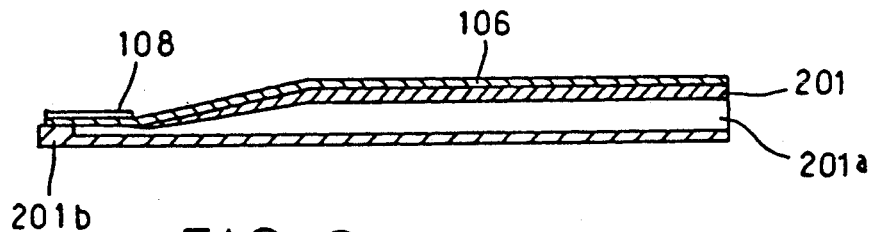
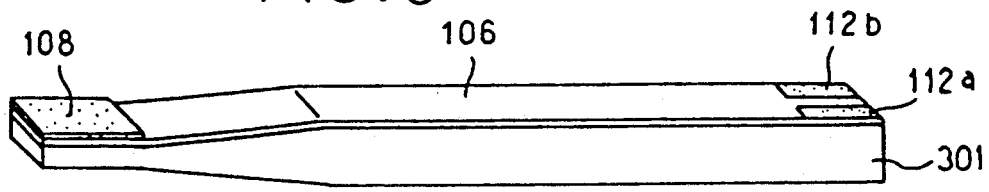
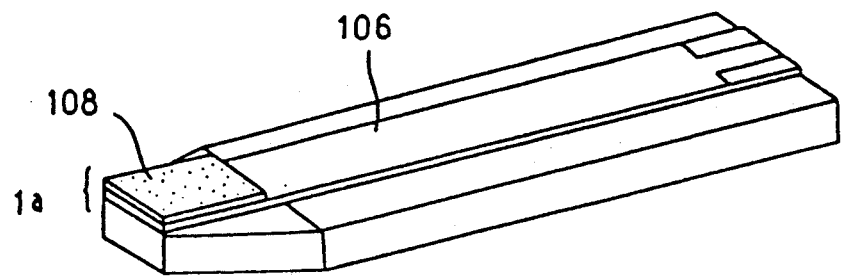

OXYGEN SENSOR

TECHNICAL FIELD

The present invention relates to an oxygen sensor which is used for detecting oxygen concentration in an exhaust gas from an internal combustion engine and the like.

BACKGROUND ART

For detecting oxygen concentration in an exhaust gas from an internal combustion engine, in order to exhibit a detecting function, an oxygen sensor is employed composed of a sensor element formed with an exothermic element for heating an oxygen concentration detecting portion being integrally laminated with the detecting portion.

Such an oxygen sensor is disclosed in, for example, the Japanese examined Patent Publication No. 36461-1988 or the Japanese Laid-open Patent Application No. 222159-1987.

As shown in FIG. 11, the former publication discloses electrodes 105 and 107 which are laminated on both faces of a solid electrolyte layer 106, which are laminated on an insulating body 101 having a gas penetrating property to form an oxygen concentration detecting portion, on which is laminated an exothermic element 103 to form a sensor element 1 of a thin plate configuration. On the other hand, as shown in FIG. 12, the latter application discloses a side face of a cylinder-shaped insulating material 110 having an air introducing hole 110a provided and a through hole 110b communicates with the air introducing hole 110a. An oxygen concentration detecting layer in which electrodes 105 and 107 are laminated on both faces of a solid electrolyte layer 106, is laminated on an exothermic element 103. Element 103 is then laminated on the insulating material 110 covering the through hole 110b to form a hollow and cylinder-shaped sensor element 1.

However, in the Japanese Patent Publication No. 36461-1988 the sensor element has a thin plate configuration, causing problems since it is weak from a view of strength to easily suffer breakage and damage due to vibration and shocks. On the other hand, Japanese Patent Application Laid-open No. 222159-1987 has a large heat capacity on account of the hollow and cylinder-shaped sensor element which has a low heating efficiency of the sensor element by the exothermic element, so that there is a problem, since it cannot exhibit its function immediately during the start-up of an internal combustion engine and the like in which rapid heating of the sensor element is required.

The present invention has taken the above circumstances into consideration, the object of which is to provide an oxygen sensor which is composed of a sensor element being strong against vibration and shocks and capable of performing rapid heating.

DISCLOSURE OF INVENTION

In order to achieve the above mentioned object, the present invention provides an oxygen sensor comprising a sensor element having a body portion and a thin portion which is thinner than the body portion, a detecting element formed at the thin portion for measuring oxygen concentration, and an exothermic element formed at the thin portion of the sensor element for heating the detecting element.

According to the above mentioned means, the sensor element has the thin portion formed to be thinner than the body portion, so that the weight of the forward end portion of the sensor element decreases, thereby the stress due to the vibration and shocks applied to a supporting and fixing portion of the sensor element decreases, and the detecting element is formed at the thin portion, thereby the heating efficiency of the sensor element by the exothermic element increases.

BRIEF DESCRIPTION OF DRAWINGS

FIG. 8(a) is an illustrative view showing another example, FIG. 8(b) is a cross-sectional view of FIG. 8(a), FIG. 9 and FIG. 10 are illustrative views showing other examples of sensor elements.

BEST MODE FOR CARRYING OUT THE INVENTION

Figure 1:
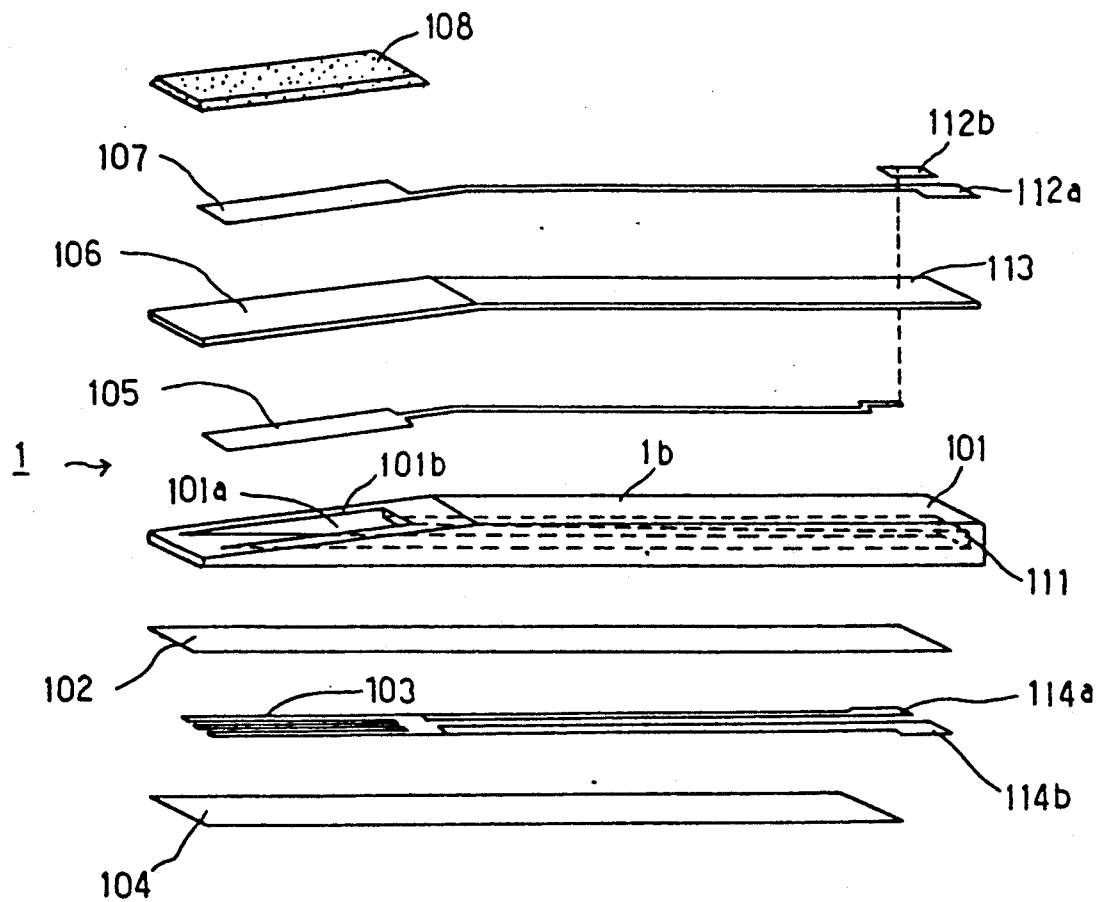
FIG. 1 is an exploded perspective view showing an example of a sensor element in an oxygen sensor of the present invention.

The present invention will be explained hereinafter according to examples shown in the figures. FIG. 1 is a development view showing an example of a sensor element in an oxygen sensor of the present invention.

In FIG. 1, 101 is a square pillar-shaped support having a through hole with both ends opened comprising alumina ceramics, zirconia ceramics or the like, and an opening end face 101a of the support 101 at the side subjected to disclosure to be exposed to an exhaust gas and makes a slant face which is continuously thinned from one face of side faces to form a thin portion 101b. When viewed in the side direction, the forward end portion of support 101 has a wedge-shaped configuration, and the other end has an air introducing hole 111 for introducing air via a body portion 1b. An exothermic element 103 mainly comprising a platinum metal material, is subjected to lamination at the face opposing the slant face of the above mentioned support 101 via an insulating layer 102 such as alumina or the like so as to completely cover the above mentioned opening portion at the slant face 101a by an exothermic portion of the exothermic element 103 as viewed in a projection drawing. Exothermic element 103, excluding terminal electrode portions 114a and 114b is laminated an insulating layer 104 comprising the same material as that of the insulating layer 102. A solid electrolyte layer 106 composed of, for example, zirconia to which yttrium is added, which has a reference electrode 105 and a measuring electrode 107 being laminated so as to coincide the opening portion at the slant face 101a of the support 101 at the side of the exhaust gas with the electrode 105 to form a sensor portion which is a detecting element 1a. The reference electrode 105 is connected with a reference electrode terminal 112b via a through hole 113 provided at the solid electrolyte 106, and the measuring electrode 107 is connected with a measuring electrode terminal 112a, respectively.

A protecting layer 108 is provided for preventing the sensing electrode 107 from direct exposure to a gas to be measured, and is a protecting layer comprising an inorganic material such as porous alumina, spinel or the like.

Hence, the support 101 is formed by injection molding or the like, and the solid electrolyte layer 106 is formed by extrusion molding or the like, and the electrode layers 105 and 107, the exothermic element 103, and the insulating layers 102 and 104 are provided by a printing method or the like, which are laminated in a state of no sintering, after which simultaneous sinter is carried out to form the sensor element.

Figure 2:
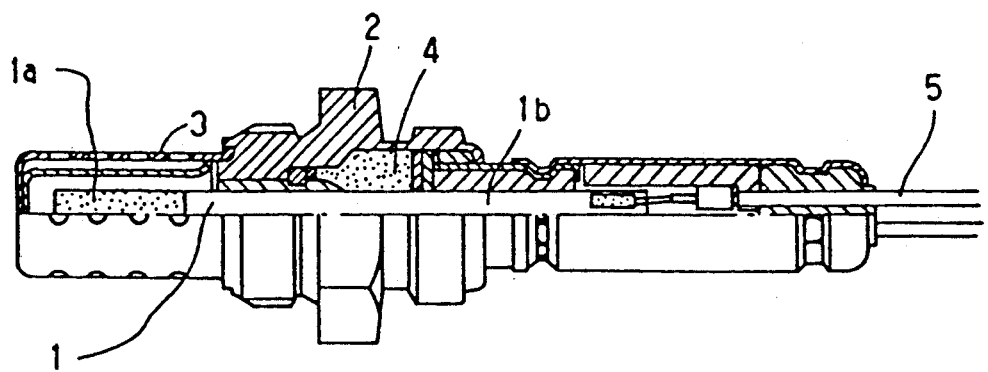
FIG. 2 is a partial cross-sectional view of the oxygen sensor provided with the above mentioned sensor element.

Incidentally, the protecting layer 108 is formed by flame spray coating of powder of a raw material after sintering of the above mentioned sensor element. FIG. 2 is a partial cross-sectional view of an oxygen sensor into which the sensor element formed by the above mentioned method is incorporated.

In FIG. 2, 1 is the sensor element, and 2 is a housing having a protecting cover 3 for preventing the sensor portion 1a of the sensor element 1 from direct exposure to the exhaust gas, in which the sensor element 1 is incorporated into the housing 2 to be fixed by means of a method of thermal caulking or the like via a powder material 4 such as talc or the like. Further, a lead wire 5 is connected with the terminal electrode portion of the sensor element 1 by means of brazing or the like, and the lead wire 5 is pulled out to the outside of the oxygen sensor body.

Next, with respect to the above mentioned example, its function will be explained.

In the present invention, the sensor element of the oxygen sensor has the portion subjected to disclosure to be exposed to the exhaust gas provided with the thinned portion subjected to thinning in accordance with directing toward the forward end as described above, so that the heat capacity of the forward end portion which is heated by the exothermic element 103 contained in the sensor element 1 becomes small, therefore, the heating efficiency by the exothermic element 103 increases, as result, temperature rises rapid.

Figure 3:
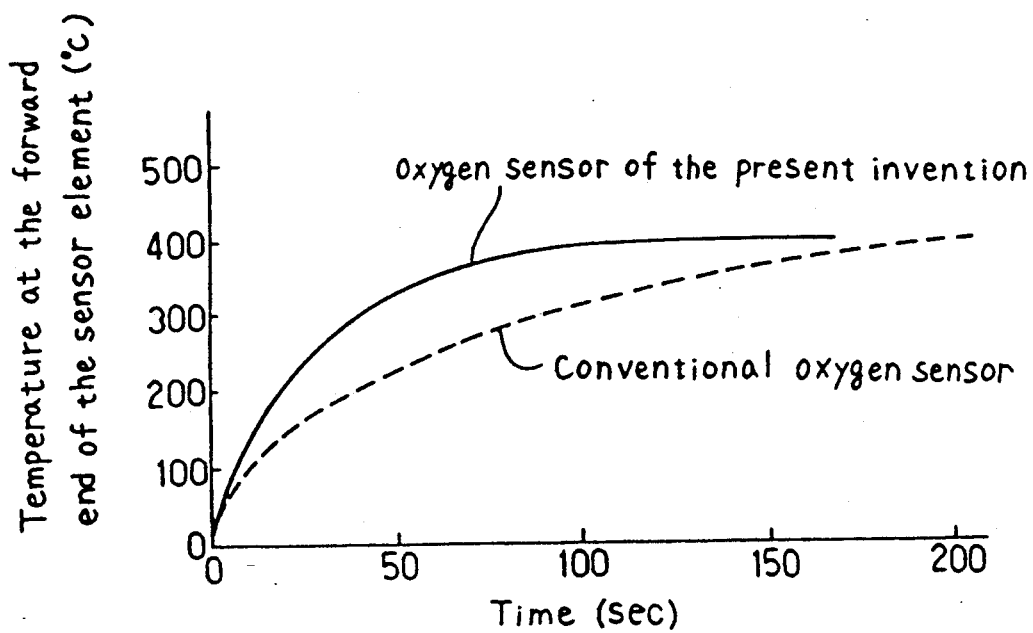
FIG. 3 is a graph showing a test result of temperature-increasing characteristics of each oxygen sensor.

FIG. 3 relates to the oxygen sensor of the present invention and a conventional oxygen sensor, which is the result of a test of temperature-increasing characteristics of the forward end portions of the sensor elements in the case of heating by the exothermic elements having the same specification contained in each sensor element.

However, with respect to the shape and size of the sensor element, for the conventional one was used a square pillar-shaped element having a width of 5 mm, a thickness of 5 mm, and a length of 60 mm, whereas for one according to the present invention was used a so-called element having the wedge-shaped forward end in which thinning was performed using a position apart from the forward end by 25 mm as a starting point in the above mentioned shape and size so as to make the forward end to have a width of 5 mm and a thickness of 2 mm.

As the result thereof, as shown in FIG. 3, it has been determined that the oxygen sensor according to the present invention has a quick temperature-rising time in reaching 400° C. That is, the time required to reach 400° C. is about half the time as compared with the conventional oxygen sensor, which provides an extreme effect.

Furthermore, the oxygen sensor of the present invention has its weight of the forward end portion of the sensor element lighter than that of the conventional one, so that the stress applied to the supporting and fixing portion of the sensor element due to vibration and shocks becomes small, thereby the sensor element becomes difficult to be destroyed.

Figure 4:
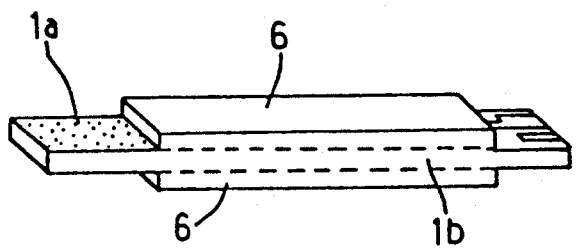
FIG. 4 is a perspective view of a sensor element, FIG. 5(a), (b), and (c) are illustrative views showing another example.

Another embodiment for the increase in the heating efficiency of the sensor element by the exothermic element and the decrease in the stress applied to the supporting and fixing portion of the sensor element is as shown in FIG. 4. That is, a reinforcing material 6 supporting portion 1b of a thin plate-shaped sensor portion may be laminated to form a thin portion. Such construction, however, results in the increase in cost due to the addition of the laminating step of the reinforcing material 6 as compared with the case in which thinning is performed continuously, as well as the following problems take place from a view of function. Namely, when a rapid change in temperature takes place at the sensor portion 1a due to rapid heating, rapid cooling or the like, then the body portion 1b, which has a larger heat capacity than the sensor portion 1a, cannot follow the change in temperature, so that a difference in thermal expansion is generated between the sensor portion 1a and the supporting portion 1b, and the stress caused thereby is concentrated at the boundary portion thereof permitting crack breakdown to easily take place at the boundary portion. In addition, there may be a case in which problems occur with respect to reliability in such an environment in which the rapid heating is required during the start-up.

However, by continuously thinning the wall thickness from the forward end of the sensor element 1, the concentration of the stress as described above can be relieved, and such a further effect can be obtained that an oxygen sensor which is excellent in reliability with respect to the rapid change in temperature can be obtained.

In addition, in order to satisfy the above mentioned characteristics, it is preferable to make the thickness of the body portion 1b of the sensor element 1 to be 2 to 6 mm (in case of not less than 6 mm, the temperature characteristics decrease due to increase in the heat capacity, and in case of not more than 2 mm, the incorporation property is deteriorated due to decrease in the strength), and it is desirable for the width of the body portion of the sensor element 1 to be 3 to 6 mm after taking the incorporation property into the housing 2 and the arrangement of the electrodes 105 and 107 and the exothermic element 103 and the like into consideration, as well as for the length of the wedge-shaped portion at the forward end of the sensor element 1 to be 10 to 30 mm from a view of the characteristics of the oxygen sensor.

Incidentally, the above mentioned sensor element 1 has been square pillar-shaped, which may be polygonal pillar-shaped, and for example, even in the case of such supports 401 of a cylinder or a ellipsoidal cylinder shape as shown in FIG. 5(a), (b), and (c), the same effect can be obtained.

Figure 6:
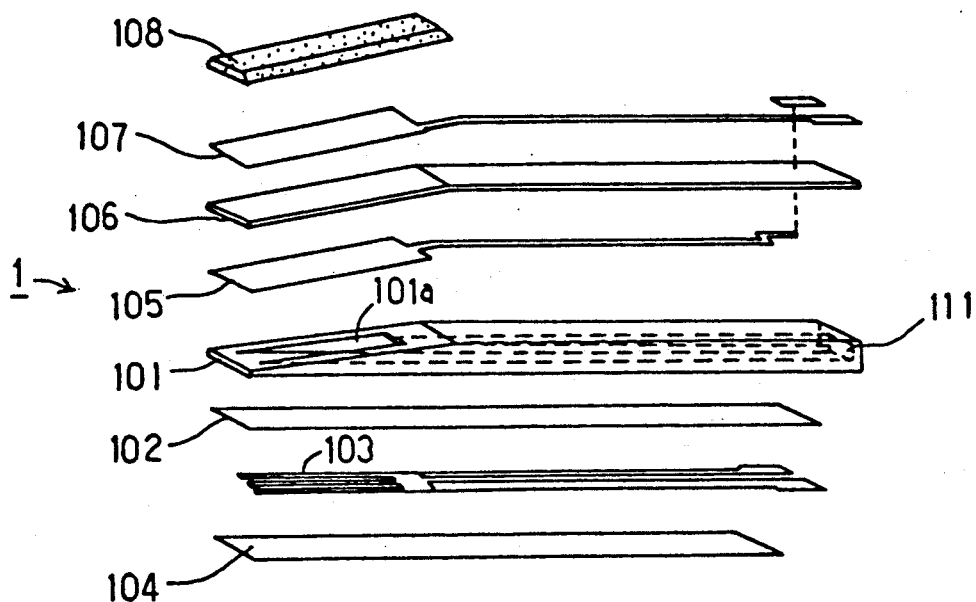
FIG. 6 and FIG. 7 are exploded perspective views showing other examples of sensor elements.
Figure 7:
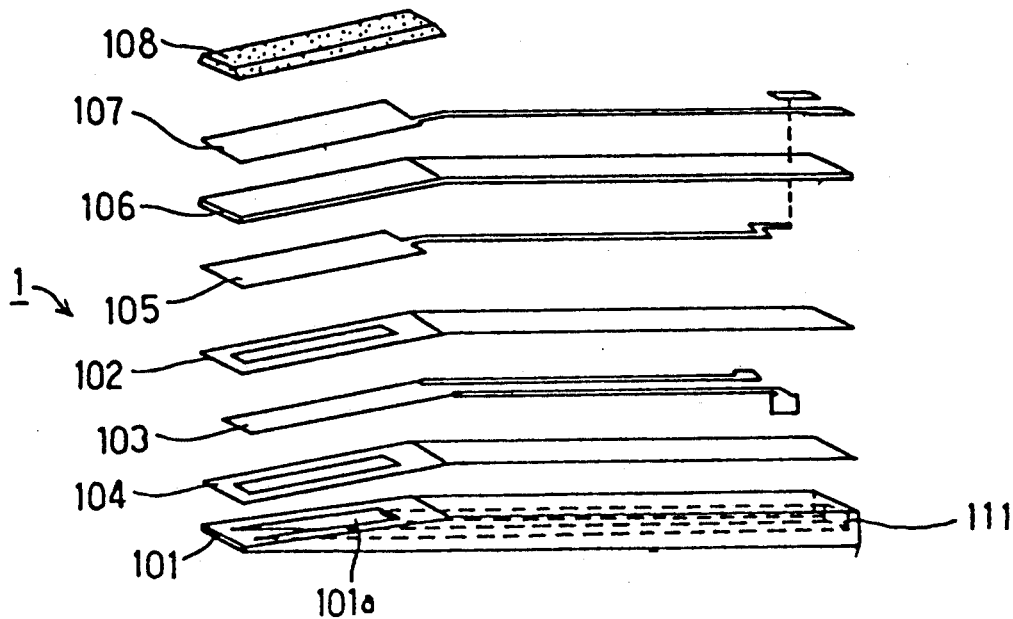
Figure 11:
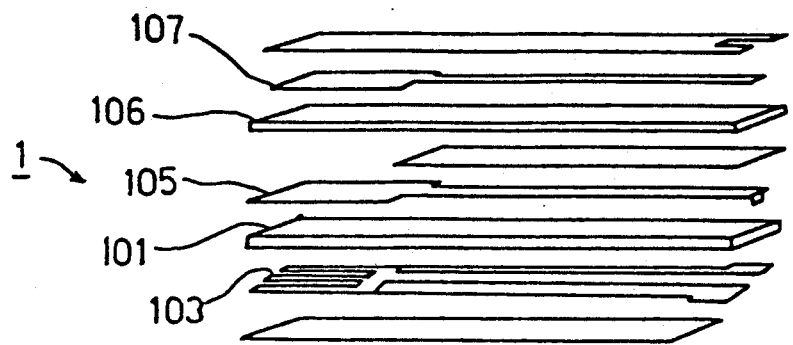
FIG. 11 and FIG. 12 are exploded perspective views of sensor elements in conventional oxygen sensors.
Figure 12:
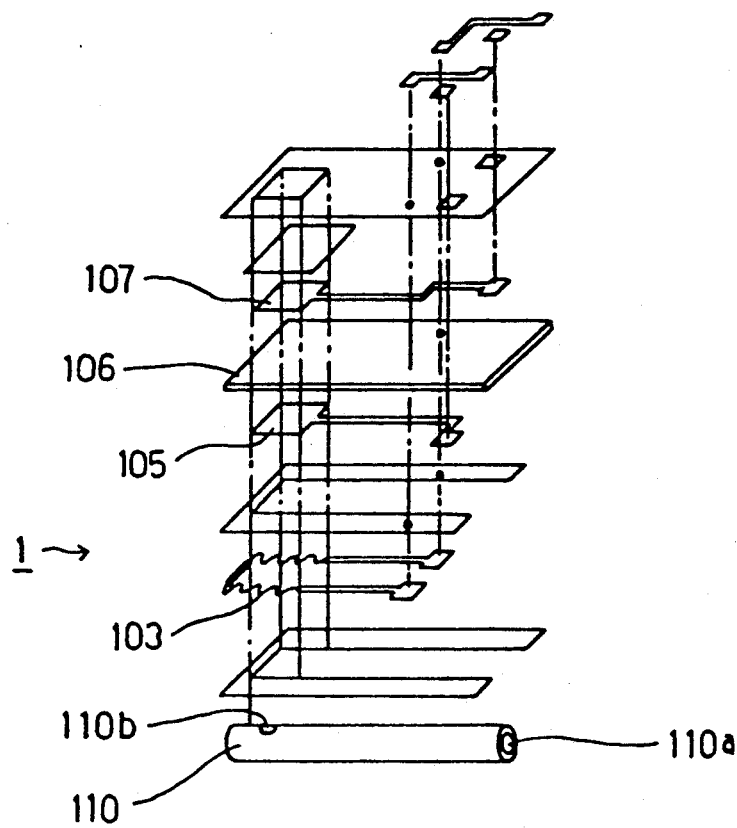

FIG. 6 and FIG. 7 show other examples of the sensor element of the present invention.

In FIG. 6, a reference electrode 105 and a measuring electrode 107, which are provided at a solid electrolyte layer 106, are arranged so as to cover not only an opening portion at a slant face 101a of a support 101 but also the whole part of the slant face, wherein the electrode layers 105 and 107 which are excellent in thermal conductivity are arranged at the whole part as described above, thereby the uniform heating property of the sensor element is increased, and increase in durability against heat shocks can be contemplated.

FIG. 7 is characterized by providing an exothermic element 103 and a sensor portion at the same face side of a support 101, thereby the heating efficiency of the exothermic element 103 can be further increased.

FIG. 8(a) and (b) show still another embodiment of the invention of the present application FIG. 8(a) and (b) are characterized in that one end of a body portion forms a slant face subjected to continuous thinning to be a thin plate, and a portion at which the sensing electrode and a protecting layer 108 are formed forms a planar plate shape. By adopting such construction, there is little thermal gradient at the measuring portion, so that detection signals can be stably obtained.

FIG. 9 shows still another example of the invention of the present application, the thin portion formed at one end of the body portion has been provided with the slant face subjected to continuous thinning from one face of side faces in the above mentioned example, however, in the present example a thinned portion is provided which is subjected to continuous thinning from the upper face or the lower face, and the thickness of the sensor element has been made constant. Owing to such construction, the heat from the exothermic element can be uniformly received by a detecting element 1a to obtain stable detection signals. FIG. 10 shows another example of the invention of the present application. FIG. 10 is characterized in that throughout both side faces of an element are formed slant faces opposing one another subjected to continuous thinning from one end of a body portion, and at the measuring portion is provided a planar plate shape. Also in such construction, there is little thermal gradient at the measuring portion, so that stable detection signals can be obtained.

Incidentally, the heat has been mainly obtained from the platinum metal material in the above mentioned examples, however, other than the above, a heater may be available which is composed of a material of high melting temperature such as tungsten, rhenium, molybdenum and the like, or an alloy material thereof.

Moreover, the protecting layer has been formed by means of the flame spray coating of the material powder in the above mentioned examples, however, other than the above, after lamination in a state of no calcination, simultaneous calcination with a support may be carried out.

EFFECTS OF THE INVENTION

The present invention is constructed as described above, so that there are provided such effects as described hereinafter.

(1) The sensor element becomes difficult to be destroyed due to vibration and shocks, so that in addition to that the reliability of the oxygen sensor increases, the temperature-rising speed of the sensor element given by heating of the exothermic element becomes rapid, therefore, sufficient function is exhibited even in the case in which rapid heating is required during the start-up and the like.

(2) In addition, the sensor element is made to be a square pillar-shaped configuration with the forward end portion of a wedge-shaped configuration, thereby the sensor element which is strong against vibration and shocks and has a rapid temperature-rising speed can be manufactured with ease.

INDUSTRIAL APPLICABILITY

As described above, the oxygen sensor according to the present invention is used for detecting oxygen concentration in an exhaust gas discharged from an internal combustion engine.

We claim:

1. An oxygen sensor having a sensor element and an exothermic element, said sensor element comprising:
   a support element for introducing a reference gas, said support element including a body portion, said body portion having a reduced thickness portion, said reduced thickness portion having a thickness which is thinner than a thickness of a remainder of said body portion, said reduced thickness portion having an opening for the introduction of the reference gas, said opening extending through said body portion; and
   a detecting element formed at said reduced thickness portion for measuring a difference of oxygen concentration between a measured gas and said reference gas passed through said opening; said exothermic element being formed at said reduced thickness portion of said support element for heating said sensor element.

2. The oxygen sensor according to claim 1, wherein said body portion has a rod-shaped configuration and one end thereof includes the reduced thickness portion, said reduced thickness portion subjected to a reduction in thickness in accordance with a direction toward a forward end of said body portion.

3. The oxygen sensor according to claim 1, wherein said body portion is composed of an element having a square pillar-shaped configuration in which a forward end portion thereof is made to be a wedge-shaped configuration defining said reduced thickness portion.

4. An oxygen sensor comprising:
   an oxygen concentration detecting element for detecting oxygen concentration in an exhaust gas; and
   a sensor element which is formed by integrally laminating together with an exothermic element for heating the oxygen concentration detecting element, wherein a portion of said sensor element being exposed to the exhaust gas includes a reduced thickness portion, said reduced thickness portion being directed toward a forward end of said sensor element.

5. The oxygen sensor according to claim 4 wherein said sensor element is composed of an element having a square pillar-shaped configuration in which said forward end has a wedge-shaped configuration defining said reduced thickness portion.

6. An oxygen sensor comprising:
   a sensor element formed to be of a square pillar-shaped configuration and having a reduced thickness portion at one end thereof, said reduced thickness portion formed to be a thin plate configuration in accordance with a direction toward a forward end of said sensor element, said reduced thickness portion having an opening for the introduction of a reference gas,
   a detecting element formed at said reduced thickness portion of said sensor element for measuring a difference of oxygen concentration between a measured gas and said reference gas passed through said opening, and an exothermic element integrally formed with said sensor element for heating said detecting element.

7. The oxygen sensor according to claim 6 wherein said reduced thickness portion has one side face of the square pillar-shaped configuration which forms a slant face so as to define said thin plate configuration, said thin plate configuration tapering to a forward end thereof, and said detecting element is formed at said slant face.

8. The oxygen sensor according to claim 6 wherein said reduced thickness portion has opposing side faces which form slant faces so as to define said thin plate configuration, and said detecting element is formed at said slant face.

* * * * *